US008920305B2

(12) United States Patent (10) Patent No.: US 8,920,305 B2
Jacobs et al. (45) Date of Patent: Dec. 30, 2014

(54) VERTICALLY ORIENTED BAND FOR STOMACH

(75) Inventors: Moises Jacobs, Miami, FL (US); Moises Jacobs, III, Miami, FL (US)

(73) Assignee: Advanced Bariatric Technology, LLC, Coral Gables, FL (US)

( * ) Notice: Subject to any disclaimer, the term of this patent is extended or adjusted under 35 U.S.C. 154(b) by 0 days.

(21) Appl. No.: 11/984,452

(22) Filed: Nov. 19, 2007

(65) Prior Publication Data

US 2008/0275480 A1 Nov. 6, 2008

Related U.S. Application Data

(63) Continuation-in-part of application No. 11/797,537, filed on May 4, 2007, now abandoned.

(60) Provisional application No. 60/881,138, filed on Jan. 19, 2007.

(51) Int. Cl.
*A61F 2/00* (2006.01)
*A61F 5/00* (2006.01)
*A61B 17/122* (2006.01)

(52) U.S. Cl.
CPC ............ *A61F 5/0086* (2013.01); *A61B 17/122* (2013.01)
USPC .............................. 600/37; 606/157

(58) Field of Classification Search
USPC ............ 600/37; 606/153–157, 139, 142, 191, 606/198; 604/909
See application file for complete search history.

(56) References Cited

U.S. PATENT DOCUMENTS

| 3,766,925 A | 10/1973 | Rubricius |
| 4,274,415 A | 6/1981 | Kanamoto et al. |
| 4,390,019 A | 6/1983 | LeVeen et al. |
| 4,458,681 A | 7/1984 | Hopkins |
| 4,558,699 A | 12/1985 | Bashour |
| 4,803,985 A | 2/1989 | Hill |

(Continued)

FOREIGN PATENT DOCUMENTS

| DE | 19751733 A1 | 12/1998 |
| DE | 29822558 U1 | 2/1999 |

(Continued)

OTHER PUBLICATIONS

Office Action for U.S. Appl. No. 11/797,537 dated Jul. 16, 2009 (10 pages).

(Continued)

*Primary Examiner* — Charles A Marmor, II
*Assistant Examiner* — Carrie R Dorna
(74) *Attorney, Agent, or Firm* — Gardere Wynne Sewell LLP

(57) ABSTRACT

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

19 Claims, 5 Drawing Sheets

(56) References Cited

U.S. PATENT DOCUMENTS

| | | | |
|---|---|---|---|
| 4,950,284 A | 8/1990 | Green et al. | |
| 4,976,721 A | 12/1990 | Blasnik et al. | |
| 5,074,868 A * | 12/1991 | Kuzmak | 606/157 |
| 5,156,609 A | 10/1992 | Nakao et al. | |
| 5,163,945 A | 11/1992 | Ortiz et al. | |
| 5,226,429 A | 7/1993 | Kuzmak | |
| 5,234,454 A | 8/1993 | Bangs | |
| 5,236,437 A | 8/1993 | Wilk et al. | |
| 5,327,914 A | 7/1994 | Shlain | |
| 5,345,949 A * | 9/1994 | Shlain | 128/898 |
| 5,464,416 A | 11/1995 | Steckel | |
| 5,549,621 A | 8/1996 | Bessler et al. | |
| 5,575,802 A | 11/1996 | McQuilkin et al. | |
| 5,766,189 A | 6/1998 | Matsuno | |
| 6,179,850 B1 | 1/2001 | Goradia | |
| 6,464,710 B1 | 10/2002 | Foster | |
| 6,537,289 B1 | 3/2003 | Kayan et al. | |
| 6,572,629 B2 | 6/2003 | Kalloo et al. | |
| 6,694,982 B2 | 2/2004 | Latour | |
| 6,716,226 B2 | 4/2004 | Sixto, Jr. et al. | |
| 6,814,742 B2 | 11/2004 | Kimura et al. | |
| 6,869,438 B2 | 3/2005 | Chao | |
| 6,981,978 B2 | 1/2006 | Gannoe | |
| 7,022,126 B2 | 4/2006 | De Canniere | |
| 7,105,000 B2 | 9/2006 | McBrayer | |
| 7,135,032 B2 | 11/2006 | Akerfeldt | |
| 7,214,233 B2 | 5/2007 | Gannoe et al. | |
| 7,223,229 B2 | 5/2007 | Inman et al. | |
| 7,232,445 B2 | 6/2007 | Kortenbach et al. | |
| 7,261,725 B2 | 8/2007 | Binmoeller | |
| 7,288,100 B2 | 10/2007 | Molina Trigueros | |
| 7,338,503 B2 | 3/2008 | Rosenberg et al. | |
| 7,416,528 B2 | 8/2008 | Crawford et al. | |
| 7,645,285 B2 | 1/2010 | Cosgrove et al. | |
| 7,691,053 B2 | 4/2010 | Viola | |
| 7,758,493 B2 | 7/2010 | Gingras | |
| 7,871,416 B2 | 1/2011 | Phillips | |
| 7,892,244 B2 | 2/2011 | Monassevitch et al. | |
| 8,529,585 B2 | 9/2013 | Jacobs et al. | |
| 2002/0022851 A1 | 2/2002 | Kalloo et al. | |
| 2002/0138086 A1 | 9/2002 | Sixto et al. | |
| 2004/0097989 A1 | 5/2004 | Trigueros | |
| 2005/0119674 A1 | 6/2005 | Gingras | |
| 2005/0125014 A1 | 6/2005 | Duluco et al. | |
| 2005/0149069 A1 | 7/2005 | Bertolero et al. | |
| 2005/0197714 A1 | 9/2005 | Sayet | |
| 2005/0216042 A1 | 9/2005 | Gertner | |
| 2005/0277959 A1 | 12/2005 | Cosgrove et al. | |
| 2006/0074440 A1 | 4/2006 | Garner | |
| 2006/0157067 A1 | 7/2006 | Saadat et al. | |
| 2006/0217757 A1 | 9/2006 | Horndeski | |
| 2006/0252983 A1 | 11/2006 | Lembo et al. | |
| 2006/0264981 A1 | 11/2006 | Viola | |
| 2006/0264982 A1 | 11/2006 | Viola et al. | |
| 2007/0021761 A1 | 1/2007 | Phillips | |
| 2007/0032807 A1 | 2/2007 | Ortiz et al. | |
| 2007/0167962 A1 | 7/2007 | Gannoe et al. | |
| 2007/0213747 A1 | 9/2007 | Monassevitch et al. | |
| 2007/0265644 A1 | 11/2007 | Ichihara et al. | |
| 2008/0033457 A1 | 2/2008 | Francischelli et al. | |
| 2008/0039879 A1 | 2/2008 | Chin et al. | |
| 2008/0092910 A1 | 4/2008 | Brooks | |
| 2008/0177292 A1 | 7/2008 | Jacobs et al. | |
| 2008/0208324 A1 | 8/2008 | Glithero et al. | |
| 2008/0275480 A1 | 11/2008 | Jacobs et al. | |
| 2008/0287976 A1 | 11/2008 | Weaner et al. | |
| 2008/0319435 A1 | 12/2008 | Rioux et al. | |
| 2011/0046641 A1 | 2/2011 | Kassab et al. | |
| 2011/0190791 A1 | 8/2011 | Jacobs et al. | |

FOREIGN PATENT DOCUMENTS

| | | |
|---|---|---|
| EP | 0201344 A2 | 11/1986 |
| EP | 0220643 A2 | 5/1987 |
| EP | 1397998 A1 | 3/2004 |
| EP | 1547529 | 6/2005 |
| EP | 1600108 A2 | 11/2005 |
| EP | 1749506 A1 | 2/2007 |
| EP | 1806101 A1 | 7/2007 |
| EP | 1882451 A2 | 1/2008 |
| JP | 9289989 A | 11/1997 |
| JP | 2002085414 A | 3/2002 |
| JP | 2007044517 A | 2/2007 |
| JP | 2007097664 A | 4/2007 |
| JP | 2007159794 A | 6/2007 |
| WO | WO-98/33437 A1 | 8/1998 |
| WO | WO-99/11179 A1 | 3/1999 |
| WO | 0076432 A1 | 12/2000 |
| WO | WO-00/78234 | 12/2000 |
| WO | 02064041 A1 | 8/2002 |
| WO | 2004017839 A1 | 3/2004 |
| WO | 2006033385 A1 | 3/2006 |
| WO | 2007013995 A2 | 2/2007 |
| WO | 2008081436 A2 | 7/2008 |
| WO | 2008091537 A2 | 7/2008 |
| WO | 2008101048 A2 | 8/2008 |
| WO | WO 2011/094700 | 8/2011 |

OTHER PUBLICATIONS

Office Action for U.S. Appl. No. 11/797,537 dated Jan. 7, 2010 (9 pages).

PCT International Search Report cited in Patent Application No. PCT/US2008/000644, dated Jul. 7, 2008 (1 page).

PCT International Search Report and Written Opinion cited in Patent Application No. PCT/US2011/023205, dated Apr. 5, 2011 (13 pages).

Helmut Kapczynski, Surgical Instruments 101, An Introduction to KMedic Certified Instruments, KMedic, Inc., 1997, Northvale, New Jersey (181 Pages).

Copending U.S. Appl. No. 13/963,998, filed Aug. 9, 2013; Inventors: Jesus R. Armenteros et al.

Copending U.S. Appl. No. 14/021,720, filed Sep. 9, 2013; Inventors: Jesus R. Armenteros et al.

International Preliminary Report on Patentability cited in PCT/US2008/000644, dated Nov. 17, 2009 (4 pgs).

Written Opinion cited in PCT/US2008/000644, dated Jul. 7, 2008 (3 pgs).

International Preliminary Report on Patentability cited in PCT/US2011/094700, dated Jul. 31, 2012 (10 pgs).

Copending International Patent Application No. PCT/US2013/54435 filed Aug. 9, 2013, entitled "Polymer Overmolded Bariatric Clamp and Method of Installing"; First Named Inventor: Armenteros, Jesus R.

International Search Report cited in PCT/US2013/54435, dated Jan. 16, 2014 (2 pgs).

Written Opinion cited in PCT/US2013/54435 dated Jan. 16, 2014 (8 pgs).

An espace English abstract of JP-9289989-A, Nov. 11, 1997.
Patent Abstract of Japan of JP-2002085414-A, Mar. 26, 2002.
Patent Abstract of Japan of JP-2007044517-A, Feb. 22, 2007.
An espace English abstract of JP-2007097664-A, Apr. 19, 2007.
An espace English abstract of JP-2007159794-A, Jun. 28, 2007.
An espace English abstract of DE-19751733, Dec. 10, 1998.
Communication and Supplementary European Search Report of Ep Application No. EP11737828, Sep. 23, 2014.
Machine Translation of DE23922558 U1.

* cited by examiner

VERTICALLY ORIENTED BAND FOR STOMACH

This application is a continuation-in-part of U.S. patent application Ser. No. 11/797,537, filed May 4, 2007 now abandoned, which claims the benefit of U.S. Provisional Application No. 60/881,138, filed Jan. 19, 2007. Thus, this application also hereby claims the benefit of U.S. Provisional Application No. 60/881,138, filed Jan. 19, 2007.

BACKGROUND OF THE INVENTION

For patients whose obesity presents an immediate serious health risk, surgical procedures are available to promote weight loss. Two of the most common surgical procedures are gastric bypass and gastric band. During gastric bypass, the stomach is made smaller and food bypasses part of the small intestine. The smaller size stomach causes the patient to eat less and the bypass of the small intestines leads to less calories being absorbed by the body.

In the most common type of gastric bypass surgery, roux-en-y, a small pouch is formed at the top of the stomach using staples. The smaller stomach is connected to the middle portion of the small intestines bypassing the upper portion of the small intestines.

Devices have been developed to form the smaller stomach from the patient's original stomach. One such device is disclosed in U.S. 2002/0022851 (Kalloo et al). The Kalloo et al patent discloses a loop 80 reducing the volume of the gastric cavity. A feeder line is pulled to reduce the diameter of the loop and collapse the walls of the stomach to define a smaller pouch.

Saadat et al (2006/0157067) discloses the use of tissue anchors to form a gastric pouch acting as a restriction to the passage of fluids and food. U.S. Pat. No. 5,345,949 (Shlain) discloses a clip placed across the fundus of the stomach to restrict the inlet chamber or proximal pouch. Likewise, U.S. Pat. No. 6,869,438 (Chao) discloses a gastric partitioning clip creating a stomach pouch from the stomach to restrict the amount of food intake.

It is an object of the invention to provide a device for separating the stomach into two compartments but allowing communication between the compartments.

It is another object of the invention to provide a device for forming a smaller stomach pouch, the size of the pouch being tailored to the patient's individual circumstances.

It is another object of the invention to provide a procedure creating a small stomach pouch to limit intake of food separate from the stomach but allowing gastric juices from the excluded stomach to flow into the pouch.

It is still another object of the invention to provide a system for creating a small pouch from the main stomach that is reversible.

It is still another object of the invention to alter the production of hormones, enzymes and chemicals that affect metabolism, energy levels, hunger, digestion, absorption of nutrients, weight loss, maintenance or gain that may be affected by exclusion of the gastric fundus and body of the stomach.

These and other objects of the invention will become apparent after reading the disclosure of the invention.

SUMMARY OF THE INVENTION

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

DETAILED DESCRIPTION OF THE INVENTION

Figure 1:
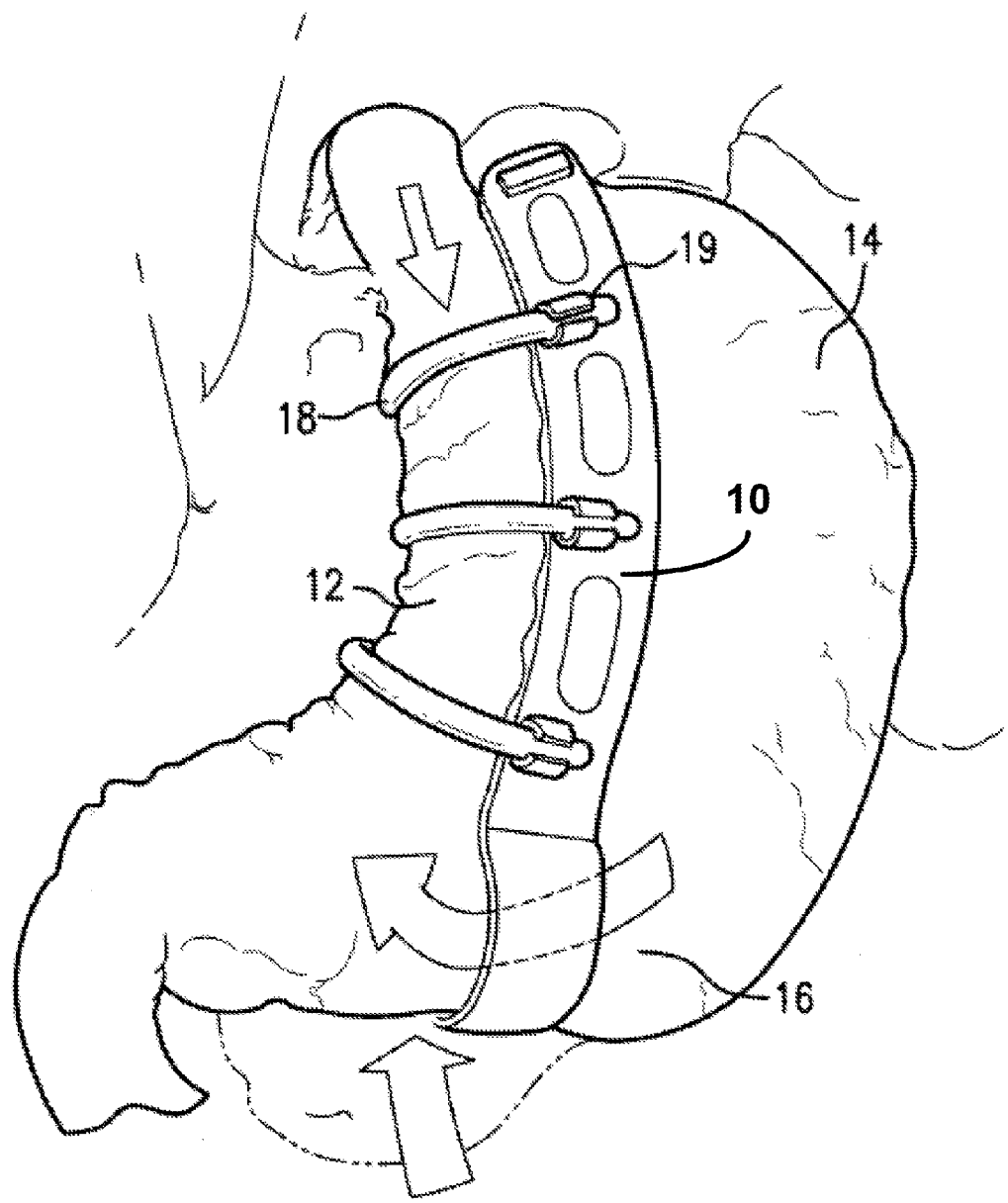
FIG. 1 is a view of the band applied to a stomach.

In FIG. 1, a stomach having the band 10 applied can be seen dividing the stomach into the pouch 12 and fundic and body area 14. Food traveling down the esophagus enters the pouch 12 and exits into the antrum. The band 10 applies pressure against the sides of the stomach to separate the stomach into the two compartments, but does not apply pressure to the stomach walls at the bottom part of the stomach. This creates a passage 16 allowing flow of gastric juices from the fundic and body area 14 into the antrum. Food will not enter the fundic and body of the stomach through this passage, however. At least one horizontal strap 18 may be used to secure the band in place. The straps may be adjustable and may apply pressure sufficient to impact the size and function of the pouch 12.

Figure 2:
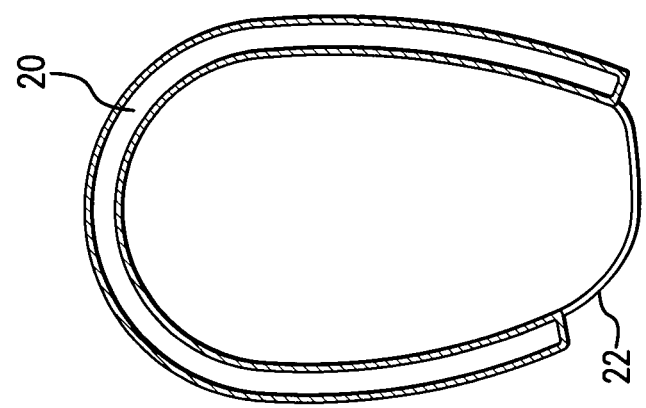
FIG. 2 is a cross-sectional view of an inflatable clamp useable with the invention.

FIG. 2 shows an embodiment of the clamp having an inflatable chamber 20 and a connecting section 22. The clamp is placed about the stomach in a vertical orientation to separate the stomach into the two compartments and inflated. The clamp may have an asymmetrically placed chamber 20, that when inflated applies pressure on the stomach to seal the two compartments from one another except for the passage 16. The connecting section 22, being not inflated, does not apply pressure to the bottom portion of the stomach, allowing for the formation of the passage 16. In addition, the clamp may have an asymmetrically placed inflatable chamber that faces the lesser curvature side of the stomach, that when inflated or deflated only alters the lumen of the vertical compartment through which the nutrients pass and does not play a role in the creation of the two compartments.

Figure 3:
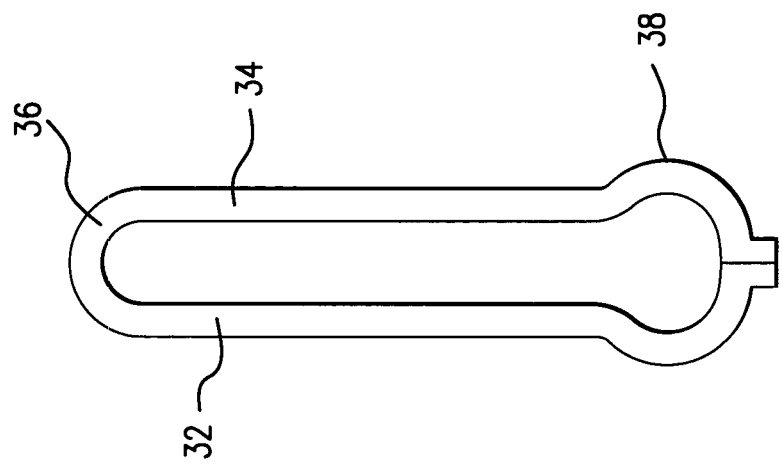
FIG. 3 is a view of a non-adjustable clamp used with the invention.

FIG. 3 shows the rigid clamp embodiment having a U portion formed by two legs 32, 34 connected by a bight portion 36. When the clamp is placed on the stomach, the bight portion fits over the top of the stomach with the legs 32, 34 applying enough pressure to collapse the walls of the stomach against one another to create the two compartments. The legs 32, 34 may or may not extend the full vertical extent of the stomach to allow for the creation of the passage 16. The legs are attached by a connector 38. When applied to the stomach, the legs serve to push the sides of the stomach together to form a complete seal but the connector allows for the formation of a passage between the two compartments. The clamp may be adjustable. The legs of the clamp may be made or adjusted to any length depending on the size of the stomach the legs can be made shorter or longer. The two legs may be connected by a magnetic coupler rather than a solid bight portion but may not be connected at all at the proximal end of the stomach. The apposition of the clamp legs about the stomach must be accomplished without sufficient force to cause ischemia of the gastric walls when the legs are closed.

Besides a clip, the vertical band may be formed as or with an inflatable balloon, as discussed with reference to FIG. 2. The orientation of the balloon is such that, upon inflation, the balloon bulges to the left to decrease the size of the compartment 12. The bottom portion may or may not be inflatable. The balloon may be attached to a tube exiting the body so that the balloon may be adjusted without the need for invasive surgery.

Figure 4:
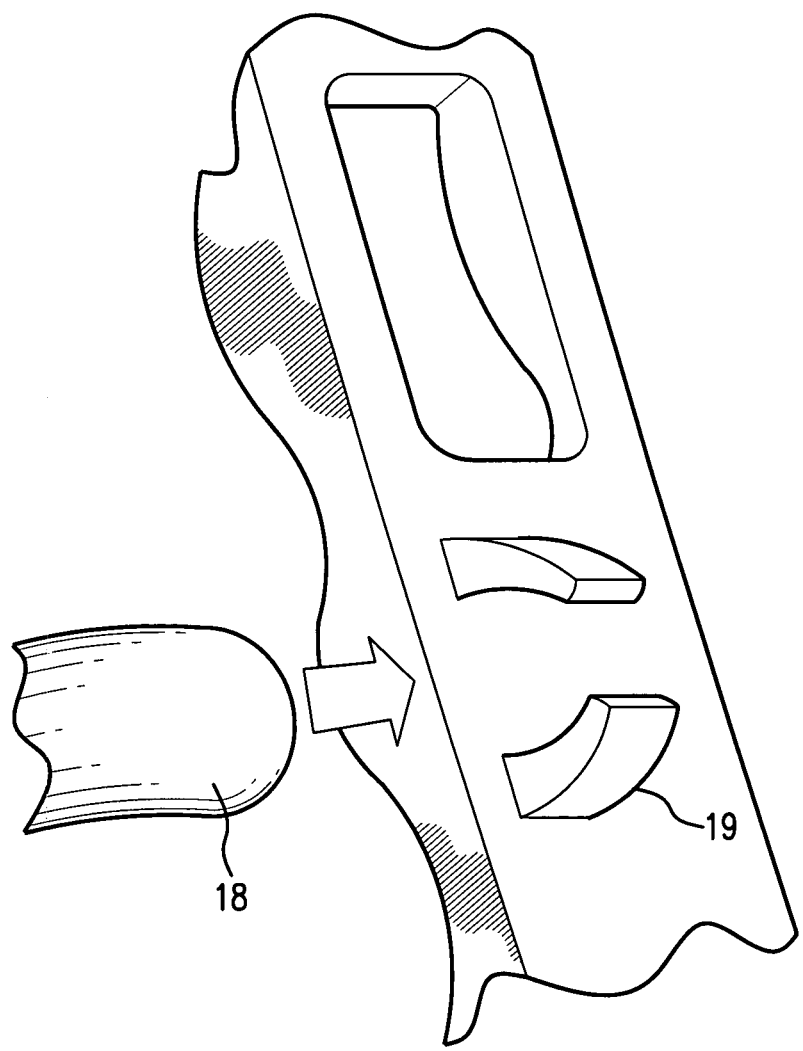
FIG. 4 is a detailed view of the strap attachment to the band.

Straps 18 can be secured to the band in any number of conventional ways. One possible way in which to secure the straps to the band is depicted in FIG. 4. The band engages and is secured by clips 19 which extend outwardly from the band. This arrangement allows the straps to be tightened by being pulled through the clip and, if desired, the straps can be released for the removal of the band. These straps may also have an inflatable chamber and may be adjustable so as to also increase or decrease the lumen of the vertical compartment through which the nutrients pass.

Figure 5:
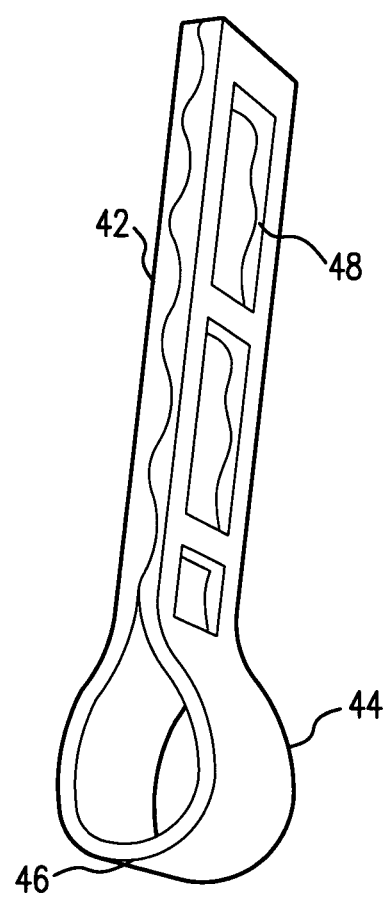
FIG. 5 is a perspective view of a second embodiment of the band.

An alternative construction of the band is seen in FIG. 5. In this embodiment, the band has a first section 42 having two parallel arms and a second section with two space members so that, when applied to a stomach, the passageway 16 is formed. The clamp itself may be curved to allow for better accommodation about the lesser curvature. The arms may be straight, curved or undulating. The surface may be smooth or serrated. The arms of the first section 42 are resiliently biased against one another and are spaced from one another in order that, when applied, the first section maintains the walls of the stomach together to separate the stomach into the first and second compartments. The pressure applied must be enough that the two compartments are formed but not so much that the walls of the stomach are damaged or compromise the blood supply. The section 44 is connected together by a section 46 acting as a hinge. This allows the arms of the first section 42 to be separated from one another in order that the band may be applied. Conversely, it is possible to have the two arms of the first section 42 hinged to one another and the two arcuate portions forming the second section 44 not connected to one another.

Figure 6:
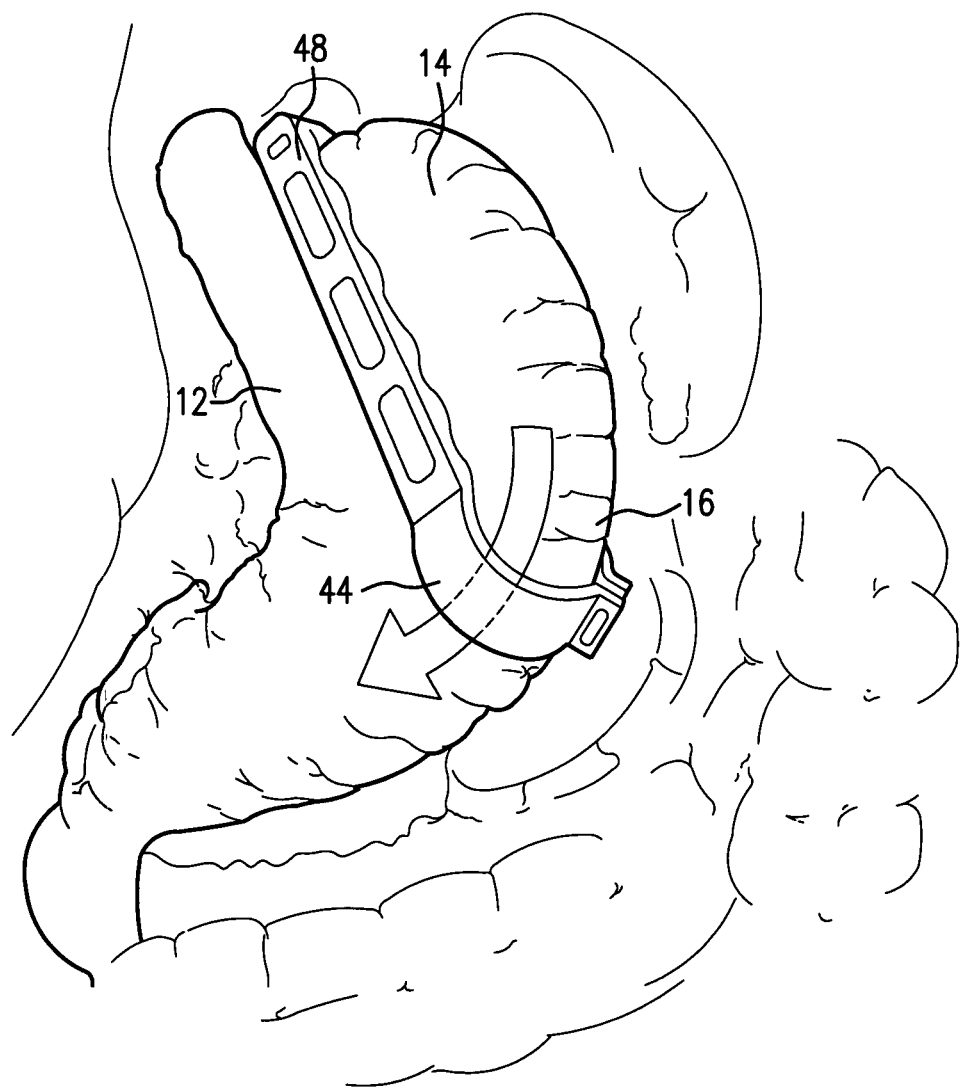
FIG. 6 is a view of the band in FIG. 5 applied to a stomach.

The band of FIG. 5 applied to stomach is seen in FIG. 6. Seen here as the first section 42 extending along the stomach to separate the stomach into two compartments, including pouch 12 and fundic and body area 14, whereas the second section has arcuate arms forming a passage 16. At least one of the arms of the first section is provided with apertures 48. The apertures, which may be large or small, allow part of the stomach wall to enter the aperture to help prevent movement of the band once it has been applied.

There are many ways in which the clamp can be applied including Natural orifice transluminal endoscopic surgery (NOTES) and the combination of NOTES and an assistant trochar placed in to the abdominal cavity. Combinations include any combination of the conventional, laproscopic, NOTES and one port techniques. The NOTES technique includes transgastric, transvaginal, transrectal, transcolonic and combinations of these. Another possibility is the one port technique wherein one port is used for the introduction of several instruments. The one port technique encompasses a one port abdominal (including umbilical), perineal, retroperitoneal approaches and combinations of these.

To facilitate application of the band, a bougie may be utilized in any suitable manner, such as placed transorally, transgastrically or transintestinally. The bougie, having a vacuum suction apparatus, collapses the stomach wall to align and help the placement the clamp. To help with alignment and placement of the clamp, the bougie may have magnets to mate with the magnets or metallic areas when the clamp is provided with such. Also, the band may be made of bioabsorbable material to negate the need to remove it.

While the invention has been described with reference to preferred embodiments, various modifications would be apparent to one of ordinary skill in the art. The invention encompasses such variations and modifications.

What is claimed is:

1. A gastric band configured to extend from a top end of a stomach to a bottom end of the stomach adjacent an antrum of the stomach to divide the stomach into a food pouch and fundic region and to provide a passage between the food pouch and fundic region, the passage formed at the bottom end of the stomach adjacent the antrum of the stomach, the gastric band comprising:

a compartment-forming section comprising a distal end of the gastric band configured to extend from the top end of the stomach towards the bottom end of the stomach, the compartment-forming section having a first arm extending a majority of a length of said gastric band and a second arm extending a majority of the length of the gastric band and spaced apart from the first arm by a first distance configured to form the food pouch and the fundic region;

a passage-forming section comprising a proximal end of the gastric band, the passage-forming section configured to extend from the bottom end of the stomach adjacent the antrum of the stomach towards the top end of the stomach, the passage-forming section configured to be positioned at the bottom end of the stomach adjacent the antrum of the stomach and configured to form the passage between the food pouch and the fundic region, the passage-forming section having a first arm extending in a direction towards and substantially collinear with the compartment-forming section and a second arm extending in a direction towards and substantially collinear with the compartment-forming section and at least partially spaced apart at a first portion by a second distance, which is greater than the first distance; and a biasing section configured to bias at least the first and second arms of the compartment-forming section to form the food pouch and the fundic region, wherein the first and second arms of the passage-forming section are arcuate and continuous, the first arm of the passage-forming section is continuous with the first arm of the compartment-forming section, and the second arm of the passage-forming section is continuous with the second arm of the compartment-forming section.

2. The gastric band of claim 1, wherein the first and second arms of the compartment-forming section are parallel.

3. The gastric band of claim 1, further comprising apertures in at least one of the first or second arms of the compartment-forming section.

4. The gastric band of claim 1, wherein at least one of the compartment-forming section and passage-forming section form a closed loop.

5. The gastric band of claim 1, wherein at least one of the compartment-forming section and passage-forming section form a U-shape.

6. The gastric band of claim 1, wherein said two arms of the passage-forming section at least partially spaced apart by said second distance are symmetrically disposed.

7. The gastric band of claim 1, wherein said compartment-forming section is substantially continuous.

8. The gastric band of claim 1, wherein the biasing section is further configured to bias the first and second arms of the passage-forming section to form the passage at the bottom portion of the stomach adjacent the antrum of the stomach and between the food pouch and the fundic region.

9. The gastric band of claim 1, wherein the biasing section is disposed towards the distal end of the gastric band.

10. The gastric band of claim 1, wherein the biasing section is disposed towards the proximal end of the gastric band.

11. The gastric band of claim 1, wherein the biasing section comprises at least one of a hinge, bight portion, and magnetic coupler.

12. The gastric band of claim 1, wherein the gastric band further comprises at least one strap coupled to the first and second arms of the compartment-forming section.

13. A gastric band, comprising:
   a first section having first and second arms spaced from one another a first distance configured to close walls of a stomach together to form a first compartment of the stomach and a second compartment of the stomach, said first section extending a majority of a length of said gastric band;
   a second section disposed at an end of the gastric band opposite the first section and configured to be positioned at a bottom portion of the stomach adjacent an antrum of the stomach, the second section having first and second arms substantially collinear with the first and second arms of the first section and at least partially spaced from one another a second distance configured to form a passage at the bottom portion of the stomach adjacent the antrum of the stomach and between the first compartment and second compartment, wherein the second distance is greater than the first distance; and
   a biasing section configured to bias at least the first and second arms of the first section to form the first and second compartments of the stomach,
   wherein the first and second arms of the second section are arcuate and continuous, the first arm of the second section is continuous with the first arm of the first section, and the second arm of the second section is continuous with the second arm of the first section.

14. The gastric band of claim 13, wherein, the first and second arms of the first section are inflatable.

15. The gastric band of claim 13, wherein said first section is substantially continuous.

16. The gastric band of claim 13, wherein the first compartment of the stomach comprises a food pouch and the second compartment of the stomach comprises a fundic region.

17. The gastric band of claim 13, wherein the passage formed by the second section provides a passage from the second compartment into the antrum of the stomach.

18. The gastric band of claim 13, wherein the biasing section is further configured to bias at least the first and second arms of the second section to form the passage at the bottom portion of the stomach adjacent the antrum of the stomach and between the first compartment and second compartment.

19. The gastric band of claim 13, wherein the biasing section comprises at least one of a hinge, bight portion, and magnetic coupler.

* * * * *